United States Patent [19]

Dozzi et al.

[11] 4,288,381

[45] Sep. 8, 1981

[54] METHOD FOR THE SYNTHESIS OF ALKOXYALANATES OF ALKALINE-EARTH METALS

[75] Inventors: Giovanni Dozzi, Milan; Salvatore Cucinella, S. Donato Mi, both of Italy

[73] Assignee: Anic S.p.A., Palermo, Italy

[21] Appl. No.: 134,093

[22] Filed: Mar. 26, 1980

[30] Foreign Application Priority Data

Apr. 4, 1979 [IT] Italy .............................. 21566 A/79

[51] Int. Cl.³ .............................................. C07F 5/06
[52] U.S. Cl. .................................................. 260/448 AD
[58] Field of Search ................................. 260/448 AD

[56] References Cited

U.S. PATENT DOCUMENTS

| | | | |
|---|---|---|---|
| 2,720,506 | 10/1955 | Caldwell et al. | 260/448 AD X |
| 3,060,216 | 10/1962 | Hamprecht et al. | 260/448 AD |
| 3,147,272 | 9/1964 | Brown et al. | 260/448 AD X |
| 3,184,492 | 5/1965 | Cole | 260/448 AD |
| 3,361,782 | 1/1968 | Ziegler et al. | 260/448 AD |
| 3,394,158 | 7/1968 | Chini et al. | 260/448 AD |
| 3,761,500 | 9/1973 | Thomas | 260/448 AD |
| 3,773,816 | 11/1973 | Honigschmid-Grossich et al. | 260/448 AD |
| 4,120,883 | 10/1978 | Sakurai et al. | 260/448 AD |

*Primary Examiner*—Helen M. S. Sneed
*Attorney, Agent, or Firm*—Morgan, Finnegan, Pine, Foley & Lee

[57] ABSTRACT

A method for the production of alkoxyalanates of alkaline earth metals is disclosed, which comprises the step of reacting an alkali metal alanate, an alkaline earth metal halide and an aluminum alcoholate.

6 Claims, No Drawings

METHOD FOR THE SYNTHESIS OF ALKOXYALANATES OF ALKALINE-EARTH METALS

This invention relates to a process for synthesising alkoxy alanates of alkaline earth metals of general formula:

$$M[AlH_{4-n}(OR)_n]_2 \cdot mB$$

in which M represents the alkaline earth metal, OR represents an alkoxyl group of a primary, secondary or tertiary alcohol in which R is an aliphatic, cycloaliphatic or aromatic radical, n is a number between 0.5 and 3.5, B is a Lewis base, m is a number between 0 and 4, and R can also contain functional groups such as OR', SR', NR'$_2$, said R' being the same as R.

The aforesaid compounds were originally described in U.S. patent application No. 960,781 filed on Nov. 15, 1978. Said application describes a method for preparing said compounds, this method comprising reacting an alanate of the alkaline earth metal with an alcohol. This reaction has the drawback of starting from alanates of alkaline earth metals, which are compounds not always available and are generally of long and laborious preparation and purification, the reaction also leading to the loss of hydride hydrogens.

It has now been discovered that it is possible to prepare the compounds of the aforesaid formula without the said disadvantages by reacting an alanate of an alkali metal with a halide of the alkaline earth metal and with alcoholates of this latter and of aluminium. This constitutes the subject matter of the present invention.

The reaction can be indicated schematically in the following manner:

$$2xM'AlH_4 + xMX_2 + yM(OR)_2 + 2yAl(OR)_3 \longrightarrow zM[AlH_{4-n}(OR)_n]_2 + 2xM'X \quad (1)$$

in which X=halogen; $z=x+y$; $n=4y/z$; M' is an alkali metal, and the other symbols have the aforesaid meanings.

Alkali metal alanates in the state in which they are produced industrially and available commercially can be used as the starting material instead of alanates of alkaline earth metals, which are not so available and require long and laborious preparation and purification.

Alkali metal alanates can be prepared by direct synthesis from their elements, or by reacting AlCl$_3$ with a hydride of the alkali metal, and in particular by reacting AlCl$_3$ with a hydride of the alkali metal in ethyl ether (reaction 2).

$$4M'H + AlCl_3 \xrightarrow{Et_2O} M'AlH_4 + 3M'Cl \quad (2)$$

In this latter case, if for example NaH is used, sodium chloride precipitates together with NaAlH$_4$ from the reaction mixture.

The process of this invention enables the mixture NaAlH$_4$—NaCl, in which the constituents are in the ratio of 1:3 as originating from reaction 2, to be used for the synthesis of 1.

The extraction of NaAlH$_4$ in its pure state can therefore be avoided. This is because NaCl is chemically inert towards the starting, intermediate and final products of the reaction, and does not influence the yield or the degree of purity of the final products. The reaction also proceeds at a good rate. The reaction proceeds in organic ether and/or hydrocarbon solvents, which are inert towards the hydride hydrogen.

The reaction is favoured by the presence of a Lewis base, in particular by tetrahydrofuran, and at the end the alkoxyalanate can contain molecules of the Lewis base used. The Lewis base can also constitute the reaction medium.

The reaction temperature can lie between $-40°$ C. and the product decomposition temperature. A temperature between $+20°$ C. and the boiling point of the reaction solvent is preferred. The use of an excess of MX$_2$ is also preferred.

At the end of the reaction, the solution of the product is separated from the metal halides by filtration, and the product is recovered by evaporating the solvent, by crystallisation, by precipitation using a non-solvent, or by other purification methods.

According to the present invention, it is also possible to replace the alcoholates of the alkaline earth metal and/or of aluminium by their potential precursors, for example a mixture of a halide of these metals and the alcoholate of an alkali metal, without this replacement altering the nature of the final alkoxyalanate of the alkaline earth metal.

Replacing for example the alcoholate of the alkaline earth metal by a mixture of one of its halides and the alcoholate of an alkali metal in the reaction leads to the synthesis of the alkoxyalanate of the alkaline earth metal in accordance with reaction 3:

$$2xM'AlH_4 + zMX_2 + 2yM'OR + 2yAl(OR)_3 \longrightarrow zM[AlH_{4-n}(OR)_n]_2 + 2zM'X \quad (3)$$

in which the symbols have the aforesaid meanings.

If however the alcoholate of the alkaline earth metal and the aluminium alcoholate are simultaneously replaced by a mixture of their halides and alkali metal alcoholates, the synthesis of the alkoxyalanate of the alkaline earth metal corresponds to reaction 4:

$$2xM'AlH_4 + zMX_2 + 2yAlX_3 + 8yM'OR \longrightarrow zM[AlH_{4-n}(OR)_n]_2 + (2x + 8y)M'X \quad (4)$$

in which the symbols have the aforesaid meanings.

Whatever the chosen type of reagent, it is important to emphasise that the operational conditions do not change substantially from those of reaction (1).

Thus, it is still possible to proceed in solvents which are inert to hydrogen hydride. Ether, aromatic and aliphatic hydrocarbon solvents can be used for this purpose.

The temperature can lie between $-40°$ C. and the product decomposition temperature. However, in order to accelerate the reaction it is preferable to operate at a temperature of between $+20°$ C. and the solvent boiling point at atmospheric pressure, and with an excess of the alkaline earth metal halide.

EXAMPLE 1

Preparation of Mg[AlH$_2$(O.i.C$_3$H$_7$)$_2$]$_2$.THF

Operating in a nitrogen atmosphere, NaAlH$_4$ (20 mmoles, in mixture with about 60 mmoles of NaCl as prepared by reacting NaH with AlCl$_3$), MgCl$_2$ (10 mmoles), Mg(O.i.C$_3$H$_7$)$_2$ (10 mmoles) and tetrahydrofuran (80 ml) are placed in that order in a 500 ml glass flask fitted with a mechanical stirrer, condenser and dropping funnel.

The stirred suspension is heated to the solvent reflux temperature, and a solution of Al(O.i.C$_3$H$_7$)$_3$ (20 mmoles) in tetrahydrofuran (50 ml) is slowly added. After the addition, the reaction mixture is kept stirred at reflux temperature for 1 hour. It is then filtered. The solution is evaporated to dryness under reduced pressure, and the oily residual product is dried under vacuum (10 hours; $1.10^{-3}$ mmHg; ambient temperature) and analysed.

Found: Al=13.5%; Mg=6.8%; H$_{act}$=10.5 meq/g.
Calculated for C$_{16}$H$_{40}$Al$_2$MgO$_5$ Al=13.9% Mg=6.3% H$_{act}$=10.4 meq/g
The yield is 92%.

EXAMPLE 2

Preparation of Ca[AlH$_{1.5}$(OCH$_2$CH$_2$OCH$_3$)$_{2.5}$]$_2$

Operating in a nitrogen atmosphere, NaAlH$_4$ (21 mmoles in mixture with about 63 mmoles of NaCl), CaCl$_2$ (52 mmoles) and tetrahydrofuran (80 ml) are placed in that order in a 500 ml glass flask fitted with a magnetic stirrer, condenser and dropping funnel. The stirred suspension is heated to the solvent reflux temperature, and a solution of NaOCH$_2$CH$_2$OCH$_3$ (35 mmoles) and Al(OCH$_2$CH$_2$OCH$_3$)$_3$ (35 mmoles) in tetrahydrofuran (60 ml) is then slowly added. After the addition, the reaction mixture is kept stirred at reflux temperature, and the Ca/Al ratio increase in the solution is checked with time. After 5 hours, the atomic Ca/Al ratio is 0.46, and after a further 2 hours is 0.49. The reaction mixture is then filtered, the solution evaporated to dryness under reduced pressure, and the residual white solid product is dried under vacuum (10 hours; $1.10^{-3}$ mmHg; ambient temperature) and analysed.

Found: Al=12.0%; Ca=8.9%; H$_{act}$=6.7 meq/g
Calculated for C$_{15}$H$_{38}$Al$_2$CaO$_{10}$ Al=11.4%; Ca=8.5%; H$_{act}$=6.4 meq/g
The yield is 80%.

EXAMPLE 3

Preparation of Ca[AlH$_2$(O.i.C$_3$H$_7$)$_2$]$_2$.2THF

Operating in a nitrogen atmosphere, NaAlH$_4$ (35 mmoles in mixture with about 105 mmoles of NaCl) in suspension in tetrahydrofuran (60 ml) and CaCl$_2$ (45 mmoles) are placed in that order in a 500 ml glass flask fitted with a magnetic stirrer, condenser and dropping funnel. The stirred suspension is heated to the solvent reflux temperature, and a suspension of Al(O.i.C$_3$H$_7$)$_3$ (35 mmoles) and NaO.i.C$_3$H$_7$ (35 mmoles) in tetrahydrofuran (100 ml) is then slowly added.

After the addition, the reaction mixture is kept stirring at reflux temperature, and the increase in the Ca/Al ratio in the solution is checked with time. After 5 hours the atomic Ca/Al ratio is 0.35, and after a further 3 hours is 0.4. Maintaining the reaction conditions unchanged, a further excess of CaCl$_2$ (5 mmoles) is added, and after 30 minutes the Ca/Al ratio is checked in the solution, and is found to be 0.51.

The reaction mixture is then filtered. The solution is evaporated to dryness under reduced pressure, and the white solid residual product is dried under vacuum (10 hours; $1.10^{-3}$ mmHg; ambient temperature) and analysed.

Found: Al=11.6%; Ca=8.7%; H$_{act}$=9.0 meq/g
Calculated for C$_{20}$H$_{48}$Al$_2$CaO$_6$: Al=11.3%; Ca=8.4%; H$_{act}$=8.4 meq/g
The yield is 88%.

EXAMPLE 4

Preparation of Ca[AlH$_2$(O.tert.C$_4$H$_9$)$_2$]$_2$.2THF.

Operating in a nitrogen atmosphere, NaAlH$_4$ (20 mmoles in mixture with about 60 mmoles of NaCl), CaCl$_2$ (20 mmoles), NaO.tert.C$_4$H$_9$ (20 mmoles), toluene (70 ml) and tetrahydrofuran (10 ml) are placed in that order in a 500 ml glass flask fitted with a magnetic stirrer, condenser and dropping funnel. The stirred suspension is heated to 80° C., and a solution of Al(O.tert.C$_4$H$_9$)$_3$ (20 mmoles) in toluene (50 ml) is slowly added. After the addition, the reaction mixture is kept stirring at 80° C., and the increase in the Ca/Al ratio in the solution is checked with time. After 4 hours, the atomic Ca/Al ratio is 0.37, and after a further 3 hours is 0.47, and correspondingly the atomic H$_{act}$/Al ratio is 1.96.

The reaction mixture is then filtered. The solution is evaporated to dryness under reduced pressure, and the residual solid product is dried under vacuum (10 hours; $1.10^{-3}$ mmHg; ambient temperature) and analysed.

Found: Al=10.4%; Ca=7.3%; H$_{act}$=7.5 meq/g
Calculated for C$_{24}$H$_{56}$Al$_2$CaO$_6$: Al=10.1%; Ca=7.5%; H$_{act}$=7.5 meq/g
The yield is 40%.

EXAMPLE 5

Preparation of Ca[AlH$_{2.5}$(O.tert.C$_4$H$_9$)$_{1.5}$]$_2$.2THF.

Operating in a nitrogen atmosphere, NaAlH$_4$ (25 mmoles in mixture with about 75 mmoles of NaCl) in suspension in tetrahydrofuran (80 ml), CaCl$_2$ (40 mmoles) and NaO.tert.C$_4$H$_9$ (15 mmoles) are placed in that order in a 500 ml glass flask fitted with a magnetic stirrer, condenser and dropping funnel. A solution of tetrahydrofuran (50 ml) and Al(O.tert.C$_4$H$_9$)$_3$ (15 mmoles) is added to the stirred suspension at ambient temperature (about 25° C.). After the addition, the reaction mixture is kept stirred at ambient temperature for about 3 hours, and is left to stand for 18 hours. The atomic Ca/Al ratio in the solution is then checked, and is found to be 0.4. The solution is again stirred at ambient temperature for a further 3 hours. The Ca/Al ratio in the solution is then 0.48.

The reaction mixture is then filtered. The solution is evaporated to dryness under reduced pressure, and the residual white solid product is dried under vacuum (10 hours; $1.10^{-3}$ mmHg; ambient temperature) and analysed.

Found: Al=11.7%; Ca=8.4%; H$_{act}$=11.1 meq/g
Calculated for C$_{20}$H$_{48}$Al$_2$CaO$_5$: Al=11.7%; Ca=8.7%; H$_{act}$=10.9 meq/g
The yield is 82%.

EXAMPLE 6

Preparation of Ca[AlH$_2$(O.i.C$_3$H$_7$)$_2$]$_2$.THF

Operating in a nitrogen atmosphere, NaAlH$_4$ (11.9 mmoles in mixture with about 36 mmoles of NaCl ), NaO.iso.C$_3$H$_7$ (47.5 mmoles), CaCl$_2$ (17.8 mmoles) and tetrahydrofuran (65 ml) are placed in that order in a 500 ml glass flask fitted with a magnetic stirrer, condenser and dropping funnel.

A solution of AlCl$_3$ (11.9 mmoles) in tetrahydrofuran (30 ml) is added to the stirred suspension at ambient temperature (about 25° C.). After the addition, the reaction mixture is kept stirring at ambient temperature for 1 hour, and the atomic Ca/Al ratio is checked in the solution and found to be 0.28. The reaction mixture is then heated to reflux temperature for 30 minutes while maintaining stirring. After this time, the Ca/Al ratio is 0.48.

The reaction mixture is filtered. The solution is evaporated to dryness under reduced pressure, and the residual white solid product is dried under vacuum (20 hours; $1.10^{-3}$ mmHg; ambient temperature) and analysed.

Found: Al=12.4%; Ca=8.8%; $H_{act}$=8.4 meq/g

Calculated for $C_{20}H_{48}Al_2CaO_6$: Al=11.3%; Ca=8.4%; $H_{act}$=8.4 meq/g

The yield is 85%.

EXAMPLE 7

Preparation of $Ca[AlH_{2.5}(O.t.C_4H_9)_{1.5}]_2.2THF$

Operating in a nitrogen atmosphere, $NaAlH_4$ (25 mmoles in mixture with about 75 mmoles of NaCl) in suspension in tetrahydrofuran (120 ml), $CaCl_2$ (30 mmoles) and $NaO.tert.C_4H_9$ (60 mmoles) are placed in a 500 ml glass flask fitted with a magnetic stirrer, condenser and dropping funnel. The stirred suspension is heated to the solvent reflux temperature, and a solution of $AlCl_3$ (15 mmoles) in tetrahydrofuran (25 ml) is then slowly added. After the addition, the reaction mixture is kept stirring at reflux temperature, and the increase in the Ca/Al ratio in the solution is checked with time. After 4 hours the atomic Ca/Al ratio is 0.3, and after a further 8 hours is 0.39. Maintaining the reaction conditions unchanged, a further excess of $CaCl_2$ (6.5 mmoles) is added, and after 6 hours the reaction mixture is filtered. The solution is evaporated to dryness under reduced pressure, and the residual solid product is dried under vacuum (10 hours; $1.10^{-3}$ mmHg; ambient temperature) and analysed.

Found: Al=10.8%; Ca=8.6%; $H_{act}$=10.1 meq/g

Calculated for $C_{20}H_{48}Al_2CaO_5$ Al=11.7%; Ca=8.7%; $H_{act}$=10.9 meq/g

The yield is 90%.

We claim:

1. A process for synthesizing alkoxyalanates of alkaline earth metals of the formula:

$M[AlH_{4-n}(OR)_n]_2.mB$ in which M represents the alkaline earth metal, OR represents an alkoxy group of a primary, secondary or tertiary alcohol in which R is an aliphatic, cycloaliphatic or aromatic radical, n is a number between 0.5 and 3.5, B is a Lewis base, m is a number between 0 and 4, and R can also contain functional groups such as OR', SR', $NR'_2$, said R' being the same as R consisting of reacting together (a) an alkali metal alanate, (b) a halide of the alkaline earth metal, (c) an alcoholate of the alkaline earth metal, and (d) an aluminium alcoholate.

2. A process for synthesizing alkoxyalanates of alkaline earth metals as claimed in claim 1 wherein the reaction is carried out in the presence of a solvent selected from ethers and/or hydrocarbons.

3. A process for synthesizing alkoxyalanates of alkaline earth metals as claimed in claim 1 wherein the reaction is carried out in the presence of a Lewis base.

4. A process for synthesizing alkoxyalanates of alkaline earth metals as claimed in claim 1 wherein the reaction is carried out at a temperature of between −40° C. and the product decomposition temperature.

5. A process as claimed in claim 1 wherein said aluminium alcoholate is replaced by its precursor comprising a mixture of an aluminium halide and an alkali metal alcoholate.

6. A process as claimed in claim 1 wherein said alkaline earth metal alcoholate is replaced by its precursor comprising a mixture of an alkaline earth metal halide and an alkali metal alcoholate.

* * * * *